(12) United States Patent
Kukita

(10) Patent No.: US 9,625,420 B2
(45) Date of Patent: Apr. 18, 2017

(54) SENSING SENSOR AND SENSING DEVICE

(71) Applicant: NIHON DEMPA KOGYO CO., LTD., Tokyo (JP)

(72) Inventor: Hiroyuki Kukita, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 222 days.

(21) Appl. No.: 14/497,349

(22) Filed: Sep. 26, 2014

(65) Prior Publication Data

US 2015/0090035 A1    Apr. 2, 2015

(30) Foreign Application Priority Data

Sep. 30, 2013  (JP) .................................. 2013-204120

(51) Int. Cl.
    *G01N 29/036*      (2006.01)
    *G01N 29/02*      (2006.01)
    *G01N 29/22*      (2006.01)

(52) U.S. Cl.
CPC ......... *G01N 29/036* (2013.01); *G01N 29/022* (2013.01); *G01N 29/222* (2013.01); *G01N 2291/0255* (2013.01); *G01N 2291/0256* (2013.01); *G01N 2291/0426* (2013.01)

(58) Field of Classification Search
CPC .. G01N 29/036; G01N 29/022; G01N 29/222; G01N 2291/0426; G01N 2291/0255; G01N 2291/0256

USPC .......................... 73/579, 61.49, 61.79, 64.53
See application file for complete search history.

(56) References Cited

U.S. PATENT DOCUMENTS

| | | | | |
|---|---|---|---|---|
| 7,938,030 B2 * | 5/2011 | Saiki | ..................... | B01L 3/5027 422/503 |
| 2007/0245810 A1 * | 10/2007 | Carter | ............... | B01L 3/502723 73/53.01 |
| 2011/0316522 A1 * | 12/2011 | Shinobu | ................... | G01N 5/02 324/109 |

FOREIGN PATENT DOCUMENTS

| | | | |
|---|---|---|---|
| JP | 2012-145566 | | 8/2012 |
| JP | 2012145566 A | * | 8/2012 |

* cited by examiner

*Primary Examiner* — Paul West
*Assistant Examiner* — Xin Zhong
(74) *Attorney, Agent, or Firm* — Jianq Chyun IP Office

(57) ABSTRACT

A sensing sensor includes a wiring board, a piezoelectric resonator, a channel forming member, a channel, an effluent channel, a capillary member, and an absorbing member. The effluent channel is disposed at a downstream side of the channel. The effluent channel is configured to discharge the sample solution inside of the channel by capillarity. The capillary member is disposed at a downstream side of the effluent channel in contact with the sample solution flowing through an inside of the effluent channel. The capillary member is configured to cause the sample solution to flow through by the capillarity. The absorbing member is disposed at a downstream side of the capillary member. The absorbing member is configured to absorb the sample solution flowing through the capillary member.

8 Claims, 8 Drawing Sheets

SENSING SENSOR AND SENSING DEVICE

CROSS-REFERENCE TO RELATED APPLICATIONS

This application claims the priority benefit of Japanese application serial no. 2013-204120, filed on Sep. 30, 2013. The entirety of the above-mentioned patent application is hereby incorporated by reference herein and made a part of specification.

TECHNICAL FIELD

This disclosure relates to a sensing sensor that senses a sensing object contained in a sample solution based on an oscillation frequency of a piezoelectric resonator such as a crystal resonator, and a sensing device that includes the sensing sensor.

DESCRIPTION OF THE RELATED ART

In a clinical field, for example, a simple inspection method referred to as a Point of care TEST (POCT) represented by self-monitoring of blood sugar level, an influenza virus test, or a similar test has been spread. The application of a sensing sensor using a Quartz Crystal Microbalance (QCM) to such test has been examined. The QCM employs a property where a resonance frequency varies according to a weight of a substance adhered to a surface of an electrode of the crystal resonator.

Japanese Unexamined Patent Application Publication No. 2012-145566 (FIG. 17 or a similar drawing) discloses a following batch type sensing sensor. The sensing sensor includes a crystal resonator with an adsorbing film that adsorbs a sensing object at one surface side. A sample solution is supplied to the crystal resonator. The sensing object is sensed based on a change in a frequency of the crystal resonator at this time. FIG. 10 illustrates an exemplary sensing sensor. A crystal resonator 91 is disposed so as to cover a through-hole 90 formed at a wiring board 9. A channel 92 for the sample solution is formed at the one side of the surface of the crystal resonator 91. The sample solution supplied from a liquid receiving portion 931 formed at a cover 93 flows from an inlet side capillary member 94 to the channel 92 and then flows through to an effluent region 96 via an outlet side capillary member 95. Reference numeral 97 denotes a film disposed at the other side of the surface of the wiring board 9 so as to cover the through-hole 90.

When measuring the sensing object, first, a buffer solution is supplied from the liquid receiving portion 931 to fill the channel 92 with the buffer solution, thus stabilizing a frequency. Next, the sample solution is supplied from the liquid receiving portion 931. This supply of the sample solution moves the buffer solution inside of the channel 92 from the outlet side capillary member 95 to the effluent region 96, and the sample solution reaches the inside of the channel 92. Thus, the sample solution flows to the inside of the channel 92 in a laminar flow. Accordingly, the buffer solution moves by being extruded to the effluent region 96 by the sample solution. When the sample solution fills the inside of channel 92, the frequency is detected. Based on the change in the frequency at this time, the sensing object in the sample solution is detected or quantitated.

For example, when the sample solution at the liquid receiving portion 931 all moves to the inlet side capillary member 94 and the supply of sample solution from the liquid receiving portion 931 is completed, the sample solution fills the inside of the channel 92. The sample solution by an amount reaching the effluent region 96 is supplied via the outlet side capillary member 95. Thus, in a state where the sample solution at the liquid receiving portion 931 all moves to the inlet side capillary member 94, the sample solution is still by a holding force of capillarity. However, the buffer solution is accumulated within the effluent region 96, and the effluent region 96 and the outlet side capillary member 95 are in contact with one another. Accordingly, the channel 92 in which the sample solution is present and the effluent region 96 in which the buffer solution is present are connected. This possibly causes the buffer solution to flow backward to the outlet side capillary member 95 and gradually move to the channel 92 side. From this phenomenon, the following is apprehended. In the channel 92, the buffer solution gradually mixes with the sample solution, and the buffer solution dilutes the sample solution, causing reduction in measurement sensitivity.

A need thus exists for a sensing sensor and a sensing device which are not susceptible to the drawbacks mentioned above.

SUMMARY

A sensing sensor according to this disclosure includes a wiring board, a piezoelectric resonator, a channel forming member, a channel, an effluent channel, a capillary member, and an absorbing member. The wiring board includes a connecting terminal to be connected to a measuring apparatus for measuring an oscillation frequency. A depressed portion is formed at one surface side of the wiring board. The piezoelectric resonator includes a piezoelectric piece and an excitation electrode disposed at the piezoelectric piece. The piezoelectric resonator covers the depressed portion. The piezoelectric resonator is secured to the wiring board such that a vibrating region is opposed to the depressed portion. The excitation electrode is electrically connected to the connecting terminal. The piezoelectric resonator includes an adsorbing film configured to adsorb a sensing object in a sample solution at one surface side of the piezoelectric piece. The channel forming member is disposed so as to cover a region at one surface side of the wiring board including the piezoelectric resonator. The channel forming member includes an injection port for a sample solution. The channel is formed between the wiring board and the channel forming member. The channel is configured to cause the sample solution supplied to the injection port to flow through from a one end side to another end side at the one surface side of the piezoelectric resonator. The effluent channel is disposed at a downstream side of the channel. The effluent channel is configured to discharge the sample solution inside of the channel by capillarity. The capillary member is disposed at a downstream side of the effluent channel in contact with the sample solution flowing through an inside of the effluent channel. The capillary member is configured to cause the sample solution to flow through by the capillarity. The absorbing member is disposed at a downstream side of the capillary member. The absorbing member is configured to absorb the sample solution flowing through the capillary member.

BRIEF DESCRIPTION OF THE DRAWINGS

The foregoing and additional features and characteristics of this disclosure will become more apparent from the following detailed description considered with reference to the accompanying drawings.

DETAILED DESCRIPTION

Figure 1:
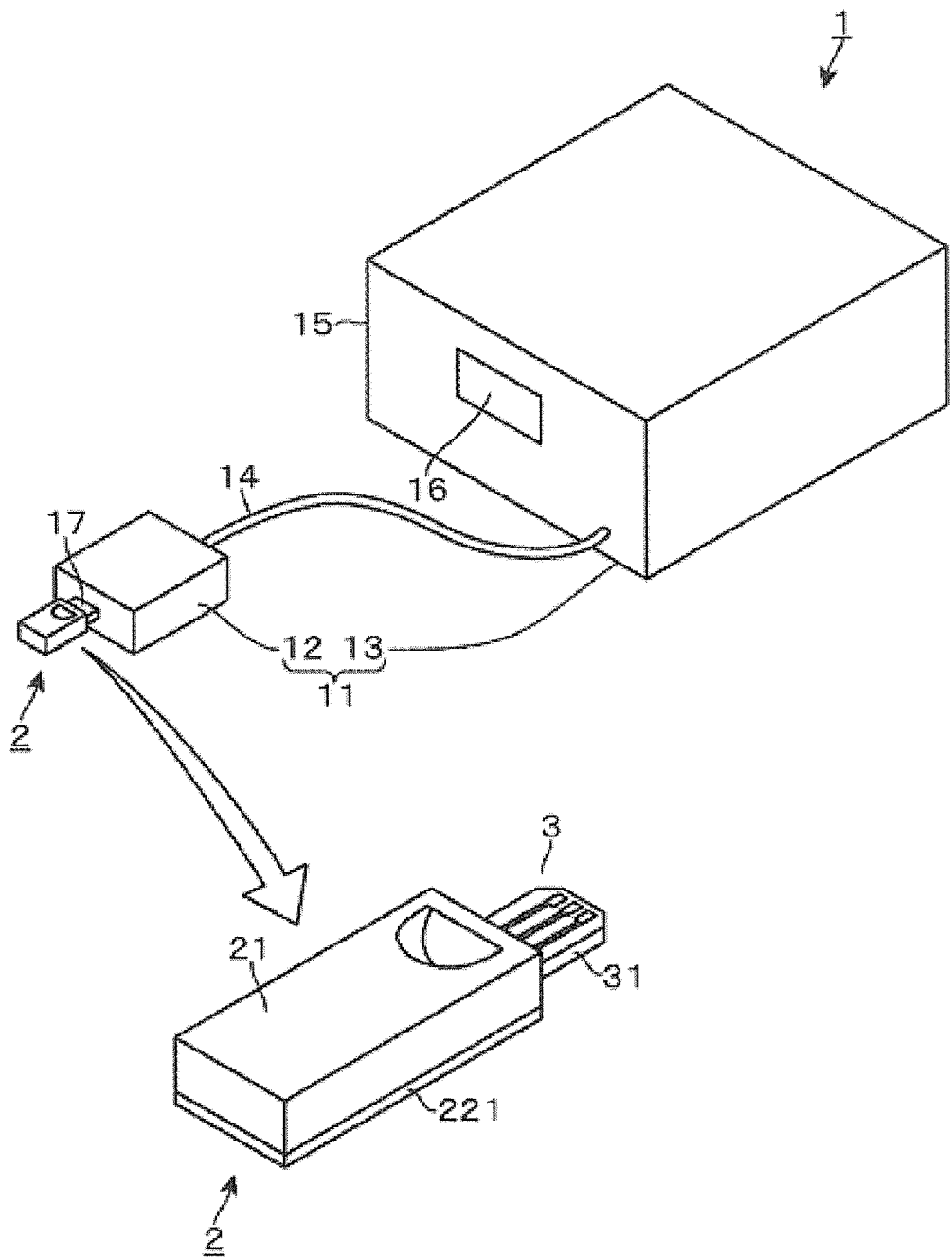
FIG. 1 is a perspective view of a sensing device according to the present disclosure.

The following description describes a sensing device 1 according to an embodiment of the disclosure. The sensing device 1 can detect, for example, presence/absence of an influenza virus in sample solution obtained from nasal cavity swab of a human so as to determine whether the human has been infected with the influenza virus or not. As illustrated in the external perspective view of FIG. 1, the sensing device 1 includes an oscillator circuit unit 12 and an arithmetic device 13. The arithmetic device 13 is connected to the oscillator circuit unit 12 via, for example, a coaxial cable 14. This oscillator circuit unit 12 and the arithmetic device 13 constitute a measuring apparatus 11. A display unit 16 is disposed at a front surface of a casing 15 of the arithmetic device 13. This display unit 16 plays a role of displaying a measurement result such as a frequency or a change amount of the frequency. A sensing sensor 2 is attachably/detachably connected to the oscillator circuit unit 12.

Figure 2:
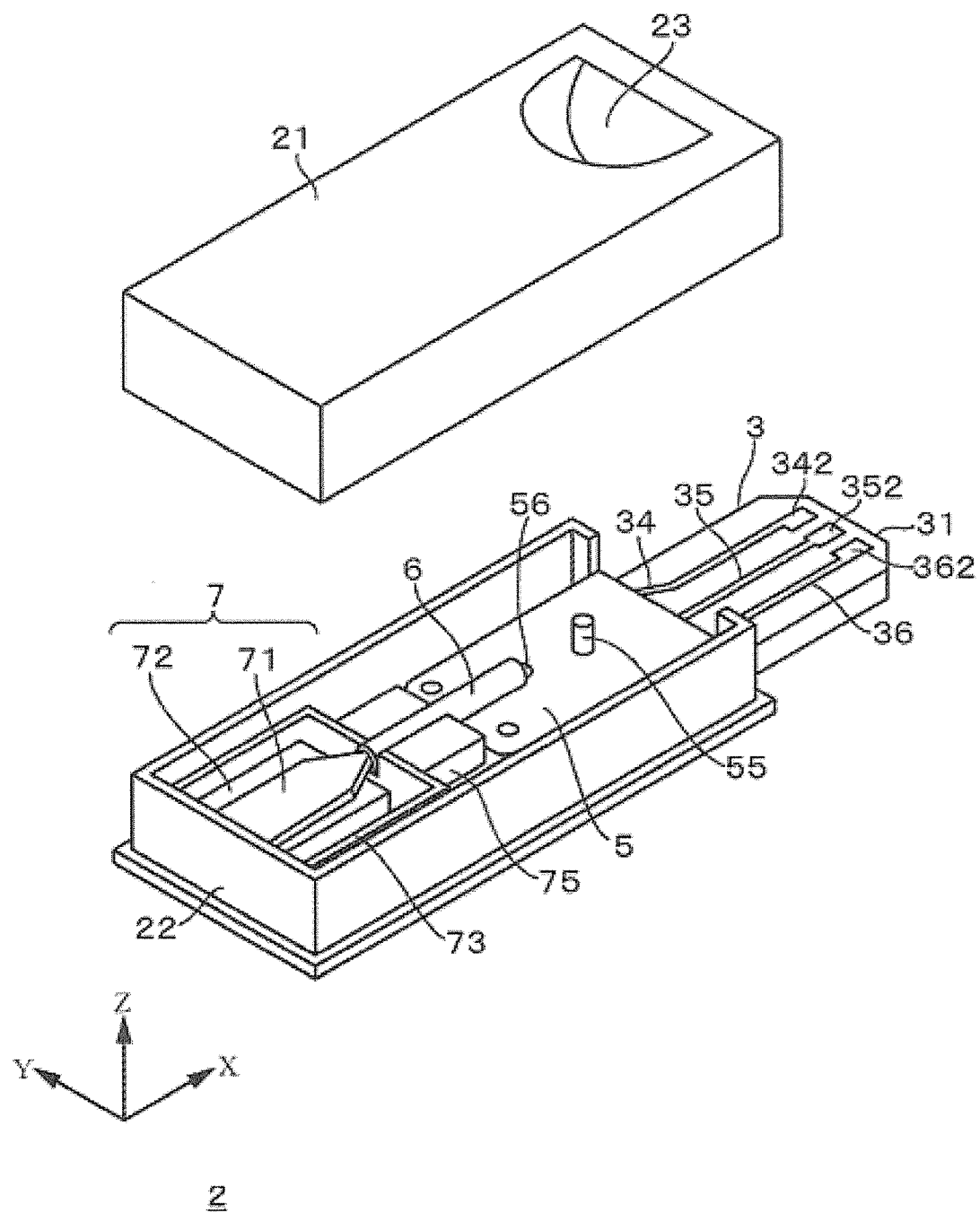
FIG. 2 is a perspective view of a sensing sensor constituting the sensing device.
Figure 3:
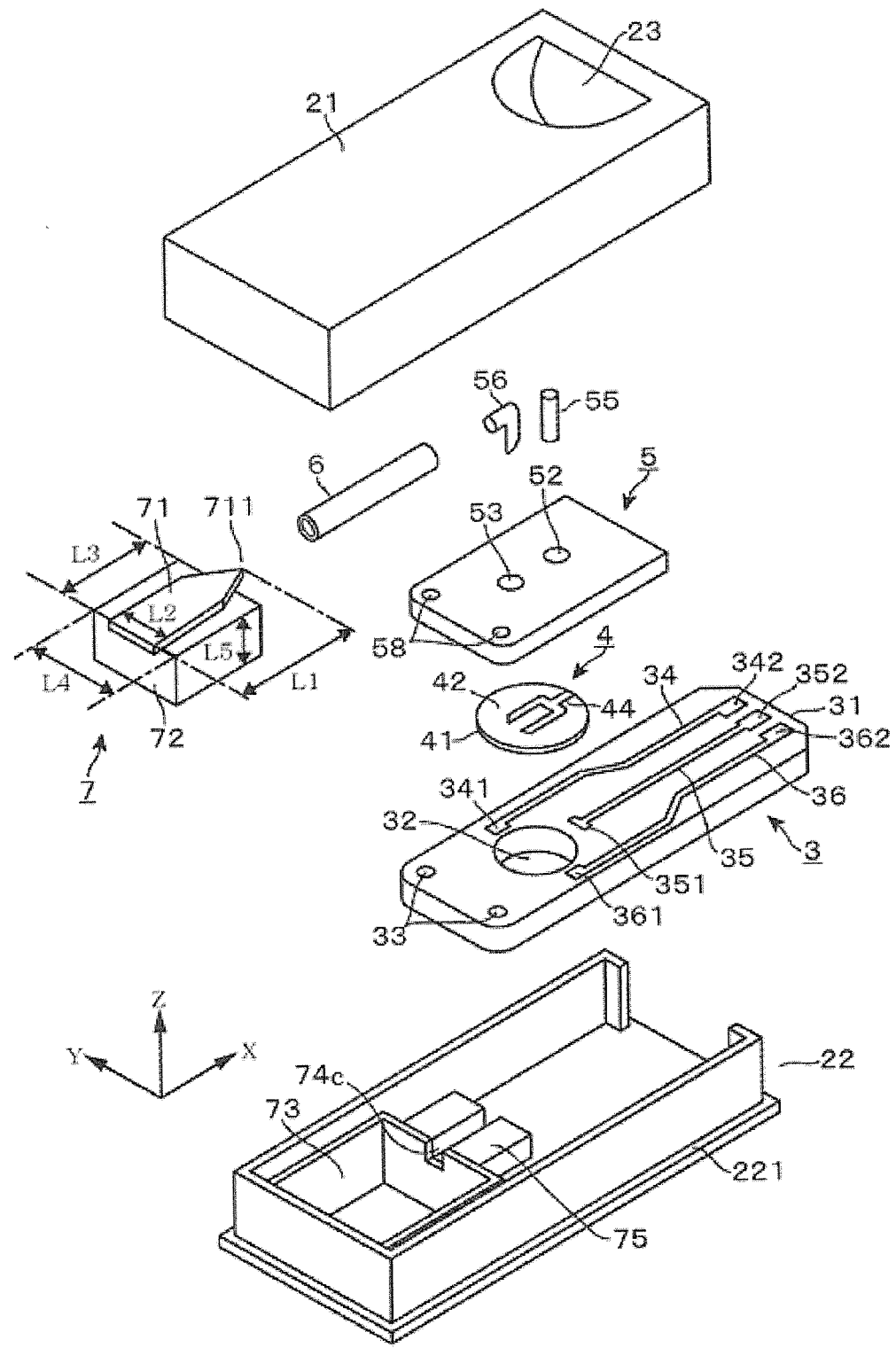
FIG. 3 is an exploded perspective view illustrating a top surface side of each part of the sensing sensor.
Figure 4:
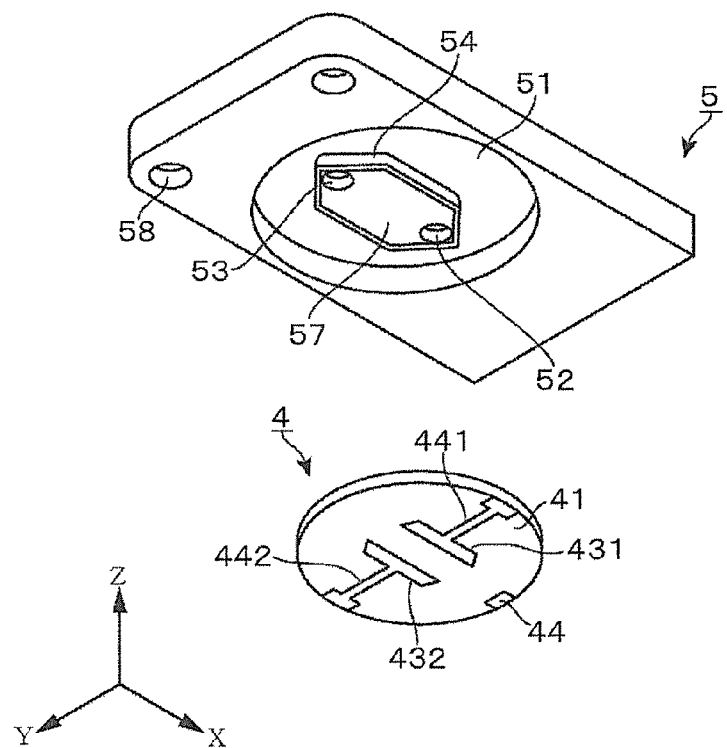
FIG. 4 is an exploded perspective view illustrating bottom surface sides of some parts of the sensing sensor.
Figure 5:
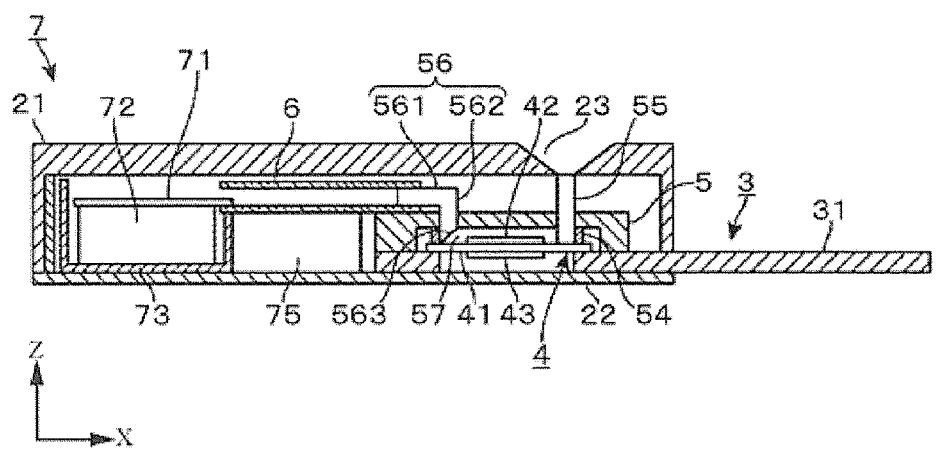
FIG. 5 is a vertical cross-sectional view of the sensing sensor.

Next, the sensing sensor 2 will be described with reference to FIG. 1 to FIG. 5. FIG. 2 is a perspective view illustrating a state where a lid body of the sensing sensor 2 (upper side cover body 21) is removed. FIG. 3 is an exploded perspective view illustrating a front side (top surface side) of each member of the sensing sensor 2. FIG. 4 is a perspective view illustrating back sides (bottom surface sides) of some members of the sensing sensor 2. FIG. 5 is a vertical cross-sectional view illustrating the sensing sensor 2 taken along a longitudinal direction (X direction in the drawing). Reference numeral 3 in the drawing denotes a wiring board. This wiring board 3 has a shape extending in a straight line direction (longitudinal direction). The wiring board 3 includes an insertion portion 31 at the other end side in the longitudinal direction. The insertion portion 31 is to be inserted into an insertion port 17 of the above-described oscillator circuit unit 12. The wiring board 3 has a through-hole 32. The through-hole 32 is covered with a bottom surface 221 of a lower side cover body 22, which will be described later. The through-hole 32 and the bottom surface 221 of the lower side cover body 22 form a depressed portion open to one surface side (front surface side) of the wiring board 3. Three wirings 34, 35, and 36 are disposed at the front surface of the wiring board 3 so as to extend from a neighborhood of an outer edge of the through-hole 32 to the insertion portion 31 side. Both end parts of these wirings 34 to 36 form terminal portions 341, 351, and 361, and connecting terminals 342, 352, and 362, respectively. The wiring board 3 also has through-holes 33.

A crystal resonator 4 is disposed at the wiring board 3. The crystal resonator 4 forms a piezoelectric resonator so as to cover the through-hole 32 from one side of the surface. A crystal element 41 of the crystal resonator 4 is, for example, formed into a circular shape. Excitation electrodes 42 and 43 are formed at the front surface side and the back surface side of the crystal resonator 4, respectively. The excitation electrode 42 at the front surface side is formed into, for example, an approximately U shape. The excitation electrode 43 at the back surface side includes two excitation electrodes 431 and 432 disposed in parallel to one another. The excitation electrode 42 at the front surface side and the excitation electrodes 431 and 432 are formed so as to be opposed to one another via the crystal element 41. A common extraction electrode 44 is disposed at the excitation electrode 42 at the front surface side. The distal end side of the extraction electrode 44 is extended to the back surface side of the crystal element 41. Extraction electrodes 441 and 442 are connected to the excitation electrodes 431 and 432 at the back surface side, respectively.

Figure 6:
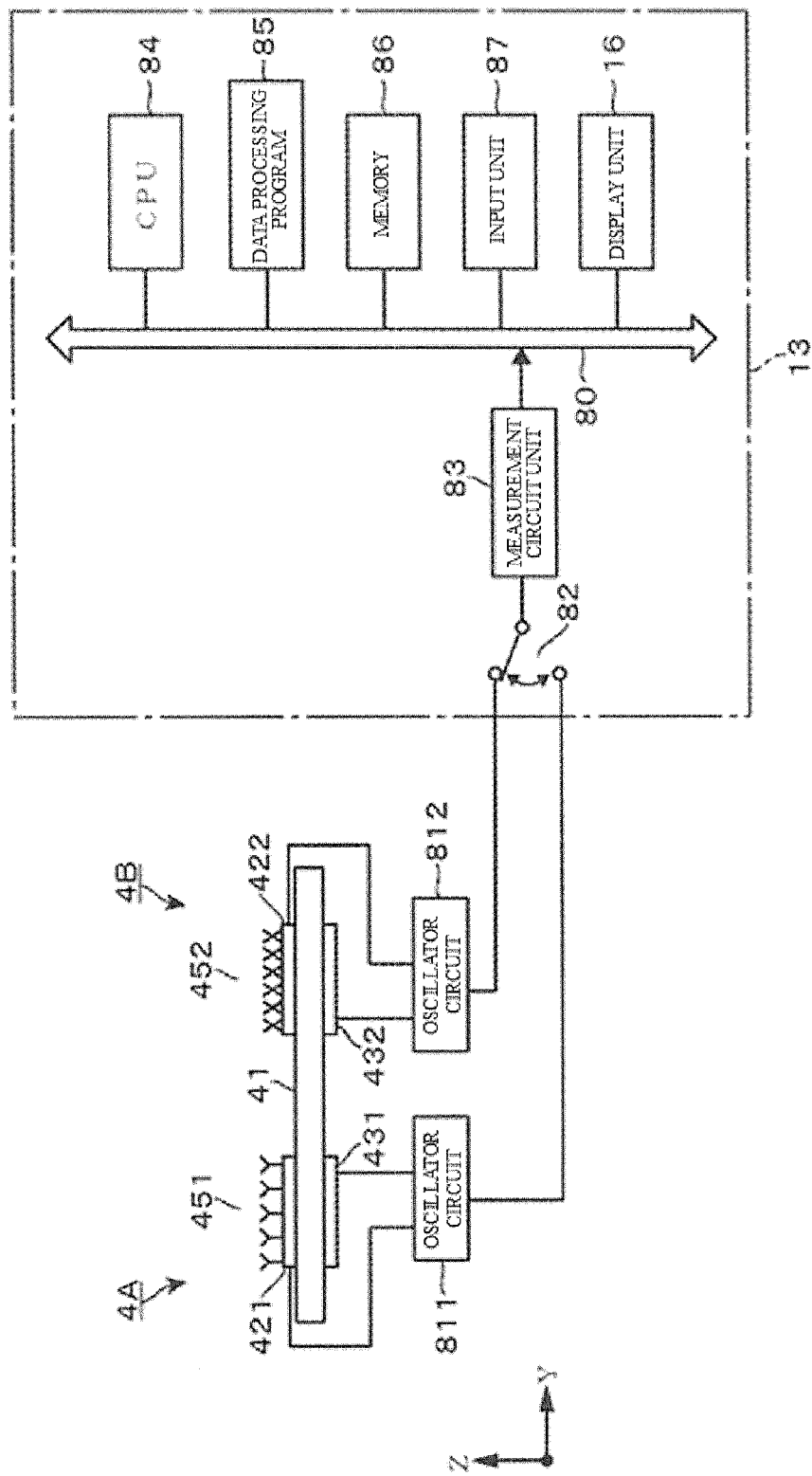
FIG. 6 is a block diagram illustrating a configuration of the sensing device.

Assume that respective regions at the excitation electrode 42 at the front surface side opposed to the excitation electrodes 431 and 432 are excitation electrodes 421 and 422 for convenience. As illustrated in FIG. 6, an adsorbing film 451 is disposed at the front surface of the excitation electrode 421. The adsorbing film 451 is constituted of an antibody that selectively combines with influenza virus, which is a sensing object. Meanwhile, an inhibiting film 452 is disposed at the front surface of the excitation electrode 422. The inhibiting film 452 inhibits combination of the influenza virus and the excitation electrode 422. Thus, the crystal element 41 and the excitation electrodes 421 and 431 constitute a first crystal resonator 4A. The crystal element 41 and the excitation electrodes 422 and 432 constitute a second crystal resonator 4B. These crystal resonators 4A and 4B are disposed such that the extraction electrode 44 superimposes the terminal portion 351 of the wiring board 3 and the extraction electrodes 441 and 442 superimpose the terminal portions 361 and 341 of the wiring board 3. Thicknesses of the respective electrodes of the crystal resonator 4 and the respective wirings of the wiring board 3 thus disposed are extremely thin. Accordingly, the peripheral edge portion of the crystal resonator 4 is in contact with the wiring board 3. The crystal resonator 4 is disposed in an approximately horizontal state with respect to the wiring board 3.

A channel forming member 5 is disposed at one side of the surface of the wiring board 3 so as to sandwich the crystal resonator 4. This channel forming member 5 is a plate-shaped component. The channel forming member 5 is formed so as to expose the other end part side, which constitutes the insertion portion 31 of the wiring board 3, and cover the one end part side at which the crystal resonator 4 is disposed. The channel forming member 5 is made of for example, synthetic resin exhibiting high self-absorption property, such as polydimethylsiloxane (PDMS). For example, plasma cleaning is conducted on the channel forming member 5 to activate the surface of the channel forming member 5 and to remove an organic matter on the surface. Then, the channel forming member 5 is bonded to the wiring board 3 as illustrated in the drawing.

As illustrated in FIG. 4, a depressed portion 51 is disposed at the back surface side of the channel forming member 5 along the outer shapes of the crystal resonator 4 and the wirings 34 to 36 such that the crystal resonator 4 and the wirings 34 to 36 fall within the depressed portion 51. This depressed portion 51 forms respective through-holes 52 and 53 at the positions superimposing the crystal resonator 4. The through-holes 52 and 53 pass through a thickness direction of the channel forming member 5. A framing portion 54 that surrounds the through-holes 52 and 53 is disposed projecting downward. This framing portion 54 is disposed so as to surround the excitation electrode 42. The respective through-holes 52 and 53 are arranged in the neighborhood of the one end side and the other end side of the framing portion 54 in the longitudinal direction of the excitation electrode 42. A region surrounded by the framing portion 54 forms a channel 57. This channel 57 has a horizontal ceiling surface, and a bottom surface of the channel 57 is constituted by the crystal resonator 4. The excitation electrodes 421 (431) and 422 (432) are disposed symmetrical to one another with respect to a line connecting the through-hole 52 and the through-hole 53. The channel forming member 5 has a through-hole 58 at a position corresponding to the through-hole 33 of the wiring board 3. The channel forming member 5 can be made of for example, a synthetic resin such as acrylic resin and a crystal, in addition to PDMS.

An inlet side capillary member 55 and an outlet side capillary member 56 are each constituted of porous capillary member. The inlet side capillary member 55 and the outlet side capillary member 56 are attachably/detachably disposed in the through-holes 52 and 53, respectively. The inlet side capillary member 55 is formed into, for example, a columnar shape while the outlet side capillary member 56 is formed into a shape where, for example, a column is flexed to an approximately L shape. For example, the inlet side capillary member 55 and the outlet side capillary member 56 are constituted by, for example, bundled chemical fibers of polyvinyl alcohol (PVA). These inlet side capillary member 55 and outlet side capillary member 56 may be constituted of cellulose or hydrophilized porous resin, which are porous bodies. The inlet side capillary member 55 covers the through-hole 52 of the channel forming member 5. The upper end side of the inlet side capillary member 55 is exposed to a liquid receiving portion 23, which will be described later, of the upper side cover body 21. The lower end side of the inlet side capillary member 55 enters in the channel 57 of the channel forming member 5.

The outlet side capillary member 56 is formed into an approximately L shape and includes a horizontal portion 561 and a vertical portion 562. The vertical portion 562 extends from this horizontal portion 561 to downward. The vertical portion 562 covers the through-hole 53 of the channel forming member 5, and the lower end side of the vertical portion 562 enters in the channel 57 of the channel forming member 5. The horizontal portion 561 is connected to an effluent channel 6, which will be described later. Further, a lower end surface 563 of the outlet side capillary member 56 is formed, for example, so as to incline upward with respect to a horizontal surface. In these capillary members 55 and 56, supply liquid flows through a void between fibers of the bundled chemical fibers by the capillarity. Accordingly, a hole between the fibers of the inlet side capillary member 55 (holes of the porous capillary member) corresponds to an injection port of a sample solution. Here, exemplary sizes of the inlet side capillary member 55 and the outlet side capillary member 56 are as described below. For example, the inlet side capillary member 55 with a diameter of, for example, 1.3 mm and a length of, for example, 4 mm is formed. The outlet side capillary member 56 with a diameter of, for example, 1.3 mm is formed. With the outlet side capillary member 56, a length of the horizontal portion 561 of, for example, 5 mm, a length of the vertical portion 562 of, for example, 4 mm, and an angle formed by the lower end surface 563 and the horizontal surface of, for example, 45 degrees is formed.

The effluent channel 6 is constituted, for example, to a pipe shape made of hydrophilic glass. The effluent channel 6 is disposed at the upper side of the channel forming member 5 extending along the longitudinal direction of the sensing sensor 2 (X direction in in the drawing). The downstream end of the horizontal portion 561 of the outlet side capillary member 56 is disposed so as to project into the inside of the effluent channel 6. For example, a glass pipe approximately with an inside diameter of 1.5 mm, a length of 10 mm, and a volume of 17 µl to 18 µl is employed as a glass pipe constituting the effluent channel 6.

An effluent absorber 7 is disposed at a downstream side of the effluent channel 6. The effluent absorber 7 absorbs and accumulates the sample solution. The effluent absorber 7 includes a capillary sheet 71 and an absorbing member 72. The capillary sheet 71 forms a capillary member. The absorbing member 72 is disposed in contact with the capillary sheet 71 and absorbs the sample solution flowing through the capillary sheet 71. The capillary member is made of a material causing the capillarity. For example, the capillary member is made of nonwoven fabric, paper, cellulose, cotton, bundled porous chemical fiber, hydrophilized porous resin, or a similar material. The capillary sheet 71 is constituted by forming the capillary members into a sheet shape. For example, when viewed in a planar surface, the capillary sheet 71 has a shape where one end side is narrower than the other end side. In this example, the capillary sheet 71 is formed into an elongated pentagonal shape. An apex 711 whose interior angle is an acute angle is disposed, so as to get through from a downstream end of the effluent channel 6 to the inside of the effluent channel 6. Accordingly, the downstream end of the effluent channel 61 is open. An exemplary size of the capillary sheet 71 is approximately a length L1 of 10 mm, a width L2 of 5 mm, and a sheet thickness of 0.5 mm to 1.0 mm.

The bottom surface of the capillary sheet 71 is disposed in contact with the top surface of the absorbing member 72. This absorbing member 72 can absorb liquid more than liquid that can be absorbed into the capillary sheet 71. For example, the absorbing member 72 is made of a porous body such as sponge made of PVA or a hydrophilic material, or a cotton-formed body. For example, the material and the shape of the absorbing member 72 are configured so as to accumulate liquid of approximately 200 µl to 300 µl, and in this example, the absorbing member 72 is formed into a rectangular parallelepiped shape. An exemplary size of the absorbing member 72 made of PVA is approximately as described below. The absorbing member 72 has a length L3 of 8 mm, a width L4 of 8 mm, a height L5 of 5 mm, a volume of 320 $mm^3$, a porosity of 0.9%, and an amount of absorbed effluent of 288 µl.

With the effluent channel 6 and the effluent absorber 7 thus constituted, as described later, the sample solution flows through the inside of the effluent channel 6 by the capillarity. When the sample solution reaches the capillary sheet 71, the sample solution moves such that the sample solution is pulled toward the capillary sheet 71 side at a greater speed than a moving speed of the sample solution passing through the effluent channel 6. This forms a gap between the capillary sheet 71 and the sample solution inside of the effluent channel 6. This effluent absorber 7 is housed in a case body 73 to prevent a leakage of liquid. For example, a cutout portion 74c is disposed at a sidewall at the effluent channel 6 side of the case body 73, so as to ensure an installation region of the effluent channel 6. The effluent channel 6 is supported in a state where positions in height and lateral directions are determined with a supporting member 75.

The upper side cover body 21 is disposed at one side of the surface of the channel forming member 5. This upper side cover body 21 is constituted by, for example, resin such as plastic. The upper side cover body 21 is formed so as to cover the channel forming member 5, the effluent channel 6, the effluent absorber 7, or a similar member. On the other hand, the lower side cover body 22 is disposed at the other side of the surface of the wiring board 3. Covering the upper side cover body 21 over the lower side cover body 22 allows the crystal resonator 4 to be secured to the wiring board 3 while covering the through-hole 32 and the through-hole 32 is covered with the lower side cover body 22. A protrusion (not illustrated) enters into the through-hole 33 of the wiring board 3 and the through-hole 58 of the channel forming member 5. In view of this, the lateral position shifting of the channel forming member 5 is reduced.

An opening portion constituted as the liquid receiving portion 23 is formed at the top surface side of the upper side cover body 21. Within this opening portion, the through-hole 52 is open. The liquid supplied from the liquid receiving portion 23 is supplied to a liquid channel 57 via holes between the fibers of the inlet side capillary member 55 (holes of the porous capillary member). An air hole (not illustrated) is formed at the upper side cover body 21. When liquid flows through the inside of the sensing sensor 2, the gases in the respective channels are extruded from the opening at the downstream end of the effluent channel 6 to the outside of the sensing sensor 2 via this air hole. With the sensing sensor 2 thus constituted, when the insertion portion 31 of the wiring board 3 is inserted into the insertion port 17 of the oscillator circuit unit 12, the respective electrodes of the crystal resonator 4 can be electrically connected to oscillator circuits 811 and 812.

Then, the following description describes respective portions disposed at the arithmetic device 13, which constitutes the sensing device 1, with reference to FIG. 6. A switch portion 82 is disposed at a latter part of the oscillator circuits 811 and 812. The switch portion 82 allows time sharing of frequency signals from the two oscillator circuits 811 and 812 and taking the frequency signals into the latter parts. Thus, oscillation frequencies at the respective vibrating regions can be concurrently obtained. Assume that an output from the first oscillator circuit 811 as a channel 1 and an output from the second oscillator circuit 812 as a channel 2. For example, one second is divided into "n" (n is an even number) and the oscillation frequencies at respective channels are sequentially obtained by processes performed at 1/n seconds. This obtains frequencies at least equal to or more than once per second, thus actually allowing obtaining frequencies at the respective channels simultaneously.

A measurement circuit unit 83 is disposed at a latter part of the switch portion 82. The measurement circuit unit 83 digitalizes the frequency signals, which are input signals, and measures oscillation frequencies at the respective channels. The following description denotes the outputs from the channels 1 and 2 as F1 and F2, respectively. The arithmetic device 13 includes a data bus 80. CPU 84, a storage unit storing a data processing program 85, a memory 86, and the above-described measurement circuit unit 83 are connected to the data bus 80. Additionally, an input unit 87, such as the above-described display unit 16 and a keyboard, is connected to the data bus 80.

The data processing program 85 obtains time-series data of the oscillation frequency "F1" and time-series data of the oscillation frequency "F2" based on signals output from the measurement circuit unit 83 and stores the time-series data to the memory 86. Simultaneous with this data acquisition operation, the data processing program 85 also operates "F1−F2", which is a difference of respective time-series data of the oscillation frequency F1 obtained from the channel 1 and the oscillation frequency F2 obtained from the channel 2 at the same time slot. The data processing program 85 obtains the time-series data of the difference data, stores the time-series data to the memory 86, and displays a graph of "F1−F2" on the display unit 16.

Figure 7A:
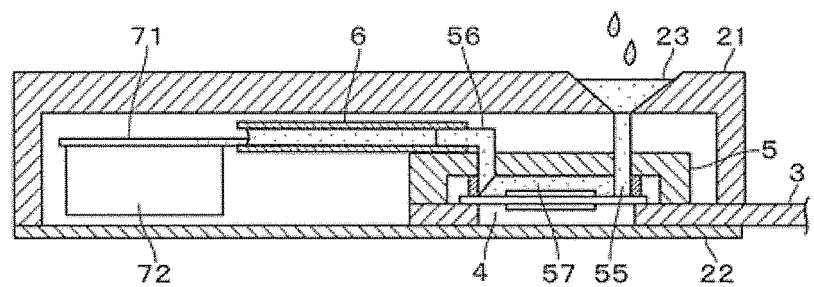
FIGS. 7A to 7D are vertical cross-sectional views illustrating states where liquid flows through the sensing sensor.

Then, the following description describes a process of determining presence/absence of an influenza virus in a sample solution using the sensing sensor 2 with reference to FIG. 7A to FIG. 8D. Note that, FIG. 7A to FIG. 8D illustrate images of liquid (buffer solution, sample solution) passing through the inside of the sensing sensor 2, and are drawn exaggeratingly more than the actual states. First, the sensing sensor 2 is connected to the oscillator circuit unit 12, and as illustrated in FIG. 7A, using an injector (not illustrated), the buffer solution that is made of, for example, a physiological saline solution and does not contain influenza virus is dropped to the liquid receiving portion 23. Here, a flow of the liquid inside of the sensing sensor 2 when the liquid is supplied to the sensing sensor 2 will be described. The liquid is absorbed into the inlet side capillary member 55 by the capillarity, flows through the inside of the capillary member 55, flows into the channel 57, and is supplied to the front surface at the one end part side of the crystal resonator 4.

Since the front surface of the crystal element 41 constituting the crystal resonator 4 is hydrophilia, an action of spreading and wetting the inside of the channel 57 works strongly. As a result, the capillarity causes the liquid to flow in the channel 57 to the other end part side of the crystal resonator 4. Subsequent to the liquid spread into the channel 57, the liquid in the inlet side capillary member 55 is extracted to the front surface of the crystal element 41 by surface tension. Thus, the liquid continuously flows from the liquid receiving portion 23 to the channel 57. Here, the capillarity means that the liquid automatically moves while spreading and wetting over a space formed by an object to which the liquid is in contact with by an interfacial tension generated with the object against the surface tension of the liquid. Accordingly, the term "capillarity" is used not only the case where the moving direction of the liquid is the vertical direction but also is the lateral direction. Since the respective films 451 and 452 formed at the excitation electrodes 421 and 422 and the electrode surfaces exhibit comparatively high hydrophilia, the liquid smoothly flows even at the surfaces of the respective electrodes 421 and 422.

When the liquid at the front surface of the crystal resonator 4 reaches the outlet side capillary member 56, the liquid is absorbed into the outlet side capillary member 56 by the capillarity, flows the inside of the capillary member 56, and soaks through the effluent channel 6. Since the effluent channel 6 is made of hydrophilic glass, the liquid is likely to spread and wet, thus the liquid passes through the effluent channel 6. Thus, the channel from the inlet side capillary member 55 to the outlet side capillary member 56 is filled with the liquid. This acts the siphon principle in addition to the capillarity. Continuously, the liquid at the liquid receiving portion 23 automatically passes through the front surface of the crystal resonator 4 and is discharged to the effluent channel 6.

The liquid inside of the effluent channel 6 passes through the inside of the effluent channel 6 to the downstream side and reaches the capillary sheet 71. As described above, when the liquid inside of the effluent channel 6 reaches the capillary sheet 71, the liquid moves to the capillary sheet 71 side at the speed faster than the moving speed of the liquid passing through the effluent channel 6. This is because of the following reason. Since the capillary sheet 71 is made of PVA, the liquid is likely to flow the capillary sheet 71 compared with the effluent channel 6 and therefore a force of absorbing the liquid is large. Here, the moving speed of the liquid inside of the effluent channel 6 is determined by a material constituting the effluent channel 6, an inside diameter of the effluent channel 6, or a similar condition. The speed that the capillary sheet 71 absorbs the liquid is determined by the material constituting the capillary sheet 71 and the shape of the capillary sheet 71 (contacted area). Accordingly, the respective material and shape are configured accordingly, such that the moving speed of the liquid inside of the effluent channel 6 and the speed that the capillary sheet 71 absorbs the liquid become appropriate speeds.

For example, the moving speed of the sample solution inside of the effluent channel 6 can be grasped by the following method. As described in the following evaluation test, the sensing sensor 2 is constituted of a transparent body. Using a colored sample solution, a passing state of the sample solution inside of the effluent channel 6 is visually checked, and conduction time of the sample solution at a certain section in the effluent channel 6 is measured. Meanwhile, the speed that the sample solution moves to the capillary sheet 71 side can be grasped by visually measuring the conduction time of the sample solution at the certain section from the one end side of the capillary sheet 71. Alternatively, by visually checking a state where the sample solution reaches the capillary sheet 71 side, is rapidly absorbed into the capillary sheet 71, and intermits in the effluent channel 6 as described later, the movement of the liquid to the capillary sheet 71 side at a faster speed than the moving speed of the liquid inside of the effluent channel 6 may be grasped.

Figure 7B:
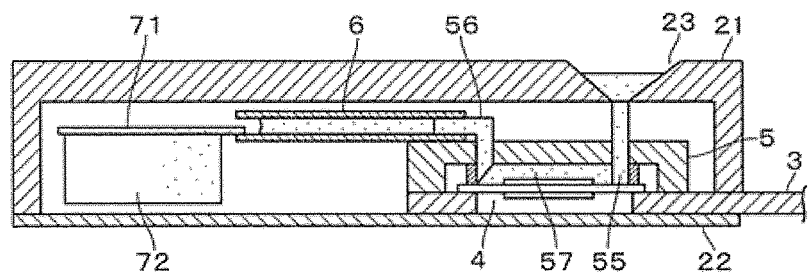

When the liquid is thus in contact with the capillary sheet 71, the liquid is promptly absorbed into the capillary sheet 71 side, the liquid passes through the inside of the capillary sheet 71 so as to expand by the capillarity and as illustrated in FIG. 7B, a state where the liquid intermits in the effluent channel 6 is formed. Since the one end side of the capillary sheet 71 is formed narrow such that the area in contact with the sample solution in the effluent channel 6 becomes small and the downstream end of the effluent channel 6 is open, an air sufficiently enters in the effluent channel 6. Thus, for example, as illustrated in FIG. 7A, the air reaches the capillary sheet 71 before the effluent channel 6 is filled with the liquid. Since the area at which the capillary sheet 71 and the liquid inside of the effluent channel 6 are in contact is small, the liquid is absorbed into the capillary sheet 71 little by little, forming a state where the liquid by the amount absorbed into the capillary sheet 71 moves from the outlet side capillary member 56 side to the inside of the effluent channel 6. Accordingly, like the case where the area at which the capillary sheet 71 is in contact with the liquid is large, the situations where an absorption speed of the liquid becomes excessively fast and the sample solution in the channel 57 is also absorbed into the capillary sheet 71 via the outlet side capillary member 56 are reduced. Accordingly, a state of dividing the liquid in the effluent channel 6 is easily formed.

When the liquid is thus divided in the effluent channel 6, the liquid at the capillary sheet 71 side is absorbed into the absorbing member 72 in contact with the capillary sheet 71 and is accumulated. Since this absorbing member 72 has larger absorbing force of liquid more than the capillary sheet 71 and can absorb large liquid amount, the liquid inside of the capillary sheet 71 promptly moves to the absorbing member 72 side. The one end side of the capillary sheet 71 projecting into the effluent channel 6 is formed narrow, but expands to the other end side. This allows the sample solution to flow expanding from the one end side of the capillary sheet 71, for example, to be absorbed into the absorbing member 72 before reaching the other end side.

Figure 7C:
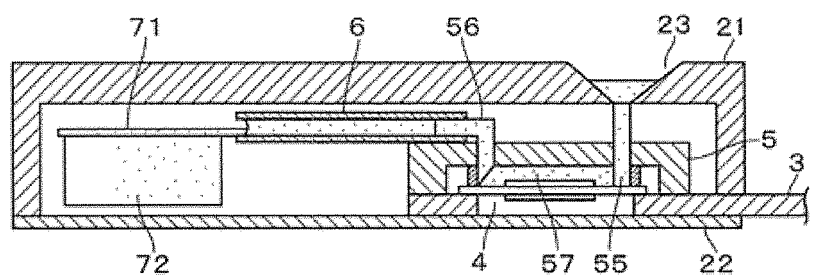
Figure 7D:
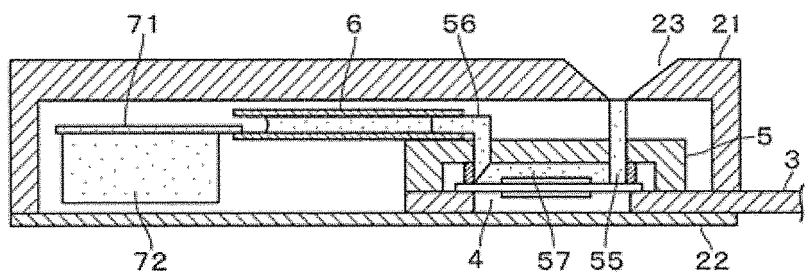

Meanwhile, the liquid remaining at the liquid receiving portion 23 attempts to flow to the effluent channel 6 by the capillarity and the siphon principle. Due to the liquid flow, the liquid remaining at the effluent channel 6 moves to the downstream and is in contact with the capillary sheet 71 again as illustrated in FIG. 7C. Thus, the division of the liquid inside of the effluent channel 6 and passing of the liquid through the inside of the effluent channel 6 are repeated. After the liquid in the liquid receiving portion 23 all passes through, a force of holding the liquid acts on the inlet side capillary member 55. This stops the passing of the liquid from the inlet side capillary member 55 to the channel 57. Accordingly, as illustrated in FIG. 7D, the liquid stops in a divided state in the effluent channel 6.

Now returning to the description of supply of the buffer solution, the buffer solution dropped to the liquid receiving portion 23 flows through the inside of the sensing sensor 2 as described above. When the buffer solution flowing in the channel 57 is supplied to the surfaces of the excitation electrodes 421 and 422, since these excitation electrodes 421 and 422 are formed symmetrically when viewed from an inlet side to the outlet side of the channel 57, the excitation electrodes 421 and 422 are uniformly affected by hydraulic pressure. Accordingly, both oscillation frequencies F1 and F2 at the first crystal resonator 4A and the second crystal resonator 4B are uniformly reduced. The supply amount of the buffer solution is set, for example, to an amount to the extent that when the buffer solution supplied to the liquid receiving portion 23 all flows into the inlet side capillary member 55, the buffer solution fills the channel 57, and is accumulated to the absorbing member 72 from the effluent channel 6 via the capillary sheet 71, for example, 50 μl.

Figure 8A:
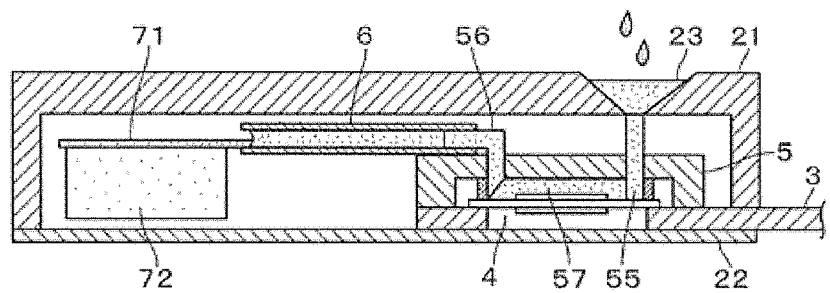
FIGS. 8A to 8D are vertical cross-sectional views illustrating states where the liquid flows through the sensing sensor.

Next, the sample solution same amount as the buffer solution is supplied to the liquid receiving portion 23. This increases pressure applied to the buffer solution absorbed into the inlet side capillary member 55. Due to the siphon principle and the capillarity, the buffer solution flows in the effluent channel 6 to the downstream side again and the sample solution is absorbed into the inlet side capillary member 55 (FIG. 8A). In FIGS. 8A to 8D, the sample solution is illustrated with gray darker than the buffer solution. The absorbed sample solution flows from the inlet side capillary member 55 into the channel 57 subsequent to the buffer solution. Then, similar to the buffer solution, the sample solution flows in the channel 57, and the channel 57 is replaced by the sample solution from the buffer solution.

In this case as well, the excitation electrodes 421 and 422 are formed symmetrically to one another when viewed from the inlet side to the outlet side of the channel. Accordingly, pressure change due to the replacement of the liquid inside of the channel 57 is uniformly applied to these electrodes 421 and 422. The oscillation frequency changes in the first crystal resonator 4A and the second crystal resonator 4B due to the pressure change are uniform to one another. In the case where the sample solution contains a measurement target object (an influenza virus in this example), the adsorbing film 451 adsorbs the influenza virus, the frequency F1 falls according to the adsorption amount, thus changing F1-F2. Thus, based on the change in F1-F2, the presence/absence of the influenza virus in the sample solution can be determined. Alternatively, a relational expression between an amount of change in the oscillation frequency difference F1-F2 and a concentration of the sensing object in the sample solution may be preliminary obtained, and the concentration of the sensing object in the sample solution may be obtained from the relational expression and the amount of change obtained by measurement.

Figure 8B:
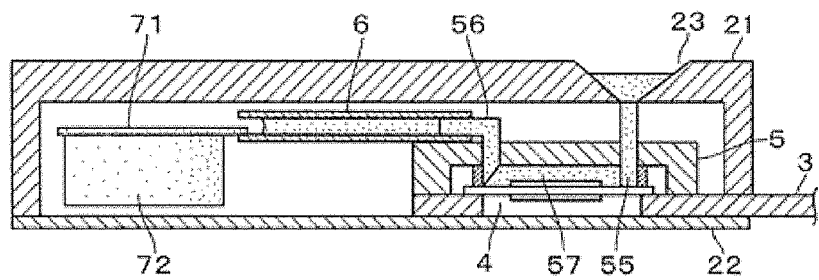
Figure 8C:
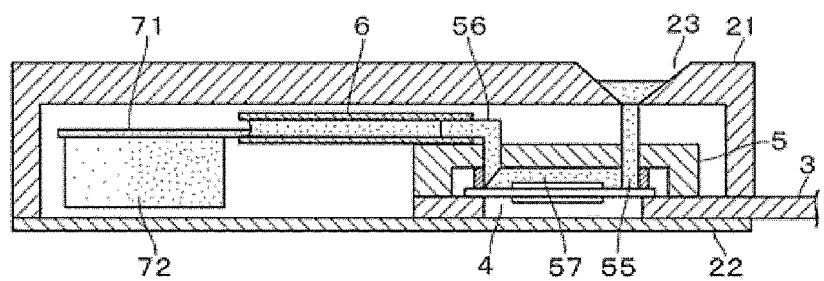
Figure 8D:
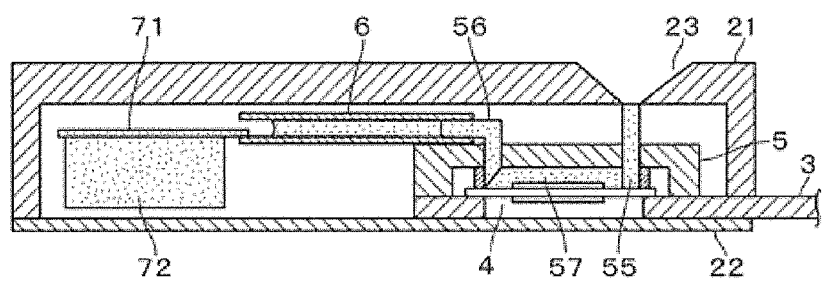

The sample solution spreading the channel 57 reaches the outlet side capillary member 56. Then, the sample solution flows into the effluent channel 6, thus keeping flowing from the inlet side capillary member 55 to the effluent channel 6. When the sample solution reaches the capillary sheet 71, as described above, a state where the sample solution intermits at the inside of the effluent channel 6 is formed (FIG. 8B). Thus, until the all sample solution supplied to the liquid receiving portion 23 flows into the inlet side capillary member 55, the division of the liquid inside of the effluent channel 6 and passing of the liquid inside of the effluent channel 6 (FIG. 8C) are repeated. After the all sample solution accumulated at the liquid receiving portion 23 flows into the inlet side capillary member 55 and the passing of the liquid to the channel 57 is stopped, the sample solution is divided and stopped at the inside of the effluent channel 6 (FIG. 8D).

With the sensing sensor 2, the sample solution flows from the injection port to the one end side and then the other end side of the excitation electrode 42 via the channel 57 at the one side of the surface of the crystal resonator 4 by the capillarity. The adsorbing film 451 disposed at the crystal resonator 4 adsorbs the sensing object contained in the sample solution. This eliminates the need for disposing a device such as a pump to flow through the sample solution. This prevents equipment from becoming large and complicated, allowing simple measurement.

The sample solution is accumulated to the absorbing member 72 via the effluent channel 6 and the capillary member disposed at the downstream of the channel 57. The capillary member is disposed in contact with the sample solution inside of the effluent channel 6. When the sample solution inside of the effluent channel 6 reaches the capillary member, the sample solution moves so as to be pulled by the capillary member. That is, when the sample solution inside of the effluent channel 6 reaches the capillary member, the sample solution moves to the capillary member side at a speed faster than the moving speed of the sample solution passing through the effluent channel 6. This forms a gap between the capillary member and the sample solution inside of the effluent channel 6.

Thus, at a phase where the all sample solution supplied to the liquid receiving portion 23 finally moves to the inlet side capillary member 55, the movement of the liquid stops in a state where the sample solution is divided at the effluent channel 6. In view of this, the capillary member of the effluent absorber 7 and the channel 57 accumulating the sample solution are separated. Accordingly, there is no region at which the buffer solution accumulated in the effluent absorber 7 and the sample solution inside of the channel 57 are in contact. This reduces a phenomenon that the buffer solution dilutes the sample solution inside of the channel 57. When the liquid reaches the capillary member, the liquid is absorbed into the capillary member side at the speed faster than the moving speed of the liquid inside of the effluent channel 6. Accordingly, the liquid is likely to flow to the capillary member side rather than the effluent channel 6. It can be said that the liquid is less likely to flow from the capillary member to the effluent channel 6 side. Accordingly, the buffer solution is less likely to flow backward from the effluent absorber 7 to the effluent channel 6. In this respect as well, the sample solution is reduced to be diluted by the buffer solution. Therefore, the sensing object in the sample solution can be always detected or quantitated at high measurement sensitivity.

Further, as described above, the sample solution is finally divided at the effluent channel 6 so the effluent absorber 7 side and the channel 57 are separated. Accordingly, in the channel 57, the sample solution on the crystal resonator 4 becomes reliably still at the channel 57. Accordingly, until an antigen-antibody reaction between the sample solution and the adsorbing film 451 is saturated, the measurement can be continued, allowing measurement at higher accuracy.

The capillary member is formed into a sheet shape. This allows decreasing the area at which the sample solution inside of the effluent channel 6 and the capillary member are in contact with, allowing forming an opening to take in air to the inside of the effluent channel 6. Therefore, before the sample solution fills the inside of the effluent channel 6, the sample solution is in contact with the capillary sheet 71. Accordingly, the sample solution inside of the effluent channel 6 can be extracted to the capillary sheet 71 side little by little, easily forming a gap between the capillary member and the liquid inside of the effluent channel 6. Provisionally, if the inside of the effluent channel 6 is filled, and the area at which the sample solution inside of the effluent channel 6 is in contact with the capillary sheet 71 becomes large, the sample solution is likely to be absorbed into the capillary sheet 71 continuously. This generates concern that a state where the division and the passing of the sample solution inside of the effluent channel 6 are repeated is less likely to occur.

Further, in the case where the capillary member is not disposed at the downstream side of the effluent channel 6, the liquid inside of the effluent channel 6 is possibly failed to be absorbed, causing the liquid inside of the effluent channel 6 to flow backward. Furthermore, if the capillary member with large absorbing force of the sample solution is disposed projecting into the inside of the effluent channel 6 so as to cover the downstream end of the inside of the effluent channel 6, when the sample solution inside of the effluent channel 6 reaches the capillary member, the liquid inside of the channel 57 is possibly absorbed into the capillary member side.

Figure 9A:
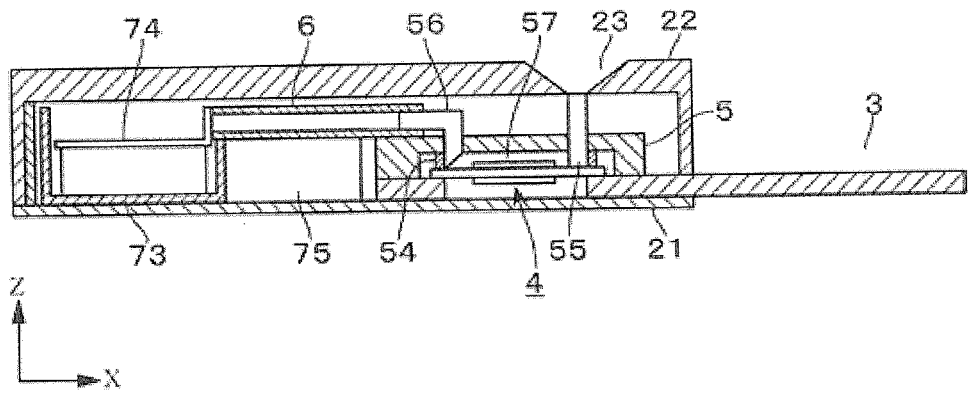
FIGS. 9A and 9B are vertical cross-sectional views illustrating another exemplary sensing sensor.

However, it is only necessary that the sensing sensor 2 of the disclosure have the following constitution. The capillary member is disposed at the downstream side of the effluent channel 6. When the sample solution inside of the effluent channel 6 reaches the capillary member, the sample solution moves to the capillary member side at the speed faster than the moving speed of the sample solution passing through the effluent channel 6. The gap is formed between the capillary member and the sample solution inside of the effluent channel 6. Therefore, depending on the shape of the effluent channel 6 and the material and the shape of the capillary member, as illustrated in FIG. 9A, the capillary sheet 74 may be disposed so as to cover the downstream end of the effluent channel 6. With this constitution as well, optimization of the pipe diameter of the effluent channel 6 and the material of the capillary sheet 74 allows forming a state where the capillary sheet 74 does not absorb the sample solution inside of the channel 57 but only the sample solution inside of the effluent channel 6 gradually moves to the capillary sheet 74 side little by little at the speed faster than the moving speed of the liquid inside of the effluent channel 6. Accordingly, when the sample solution supplied to the liquid receiving portion 23 all moves to the inlet side capillary member 55, the gap can be formed between the capillary sheet 74 and the sample solution inside of the effluent channel 6.

Further, with the above-described embodiment, a porous body such as sponge or a cotton-formed body is disposed as an absorbing member. Compared with the case where the absorbing member is not disposed, an amount of accumulated effluent can be increased. Compared with the case where the effluent region is formed at the channel forming member, the accumulated amount can be easily changed by changing the material and the size, making the design of the sensing sensor 2 easy.

As described above, when the sample solution inside of the effluent channel reaches the capillary member, as long as the sample solution moves to the capillary member side at the speed faster than the moving speed of the sample solution flowing through the effluent channel and the gap is formed between the capillary member and the sample solution inside of the effluent channel, the capillary member needs not to be always formed into a sheet shape. Furthermore, with the sensing sensor 2 illustrated in FIG. 2 to FIG. 5, to reduce the area at which the sample solution inside of the effluent channel 6 is in contact with the capillary sheet 71, the shape of the capillary sheet 71 is preferred to have a narrower shape at the one end side compared with the other end side when viewed in the planar surface and the one end side is preferred to project into the effluent channel. As such shape, a triangular shape may be employed as well as the pentagonal shape, and the one end side does not always need to be pointed. A capacity of the capillary member projecting into the effluent channel is also appropriately selected.

Figure 9B:
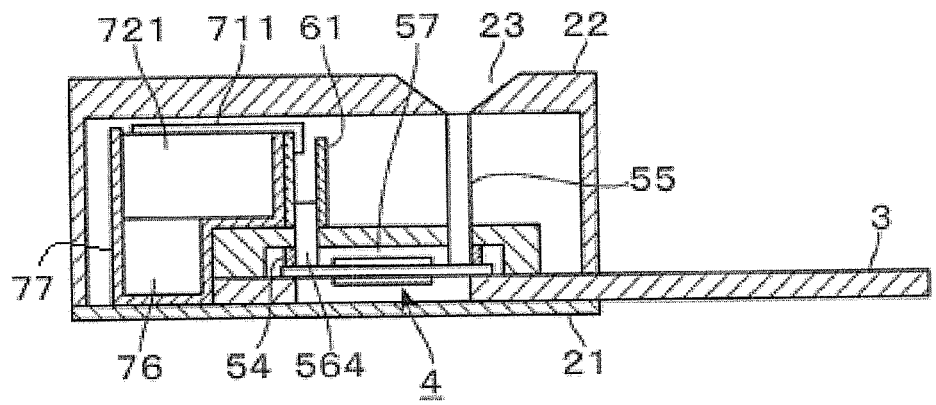
Figure 10:
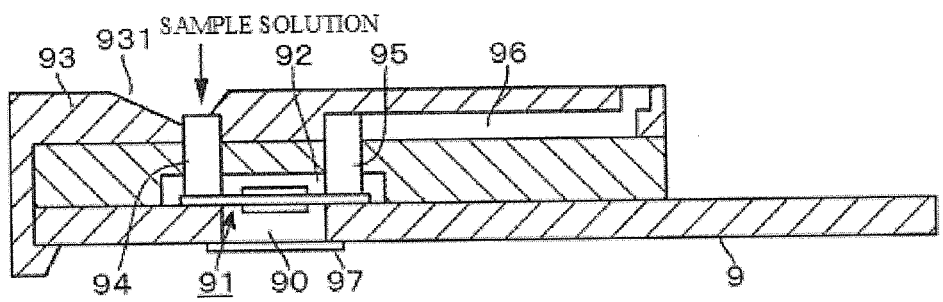
FIG. 10 is a vertical cross-sectional view illustrating a conventional example of a sensing sensor.

Further, it is only necessary that the absorbing member can absorb more liquid than the capillary member does. The capillary member and the absorbing member may be constituted of the same material. The capillary member and the absorbing member may be integrally constituted. Furthermore, as illustrated in FIG. 9B, an effluent region 76 may be formed at the lower side of an absorbing member 721. The effluent region 76 may accumulate the liquid dropped from the absorbing member 721 due to its own weight. In FIG. 9B, reference numeral 61 denotes an effluent channel, and reference numeral 564 denotes an outlet side capillary member. In this example, the effluent channel 61 and the outlet side capillary member 564 are disposed so as to vertically extend. The sample solution discharged to the inside of the effluent channel 61 flows through the inside of the effluent channel 61 upward by the capillarity. The sample solution is absorbed into the absorbing member 721 via the capillary sheet 711 disposed at the downstream end (upper end) of the effluent channel 61. The capillary sheet 711 has one end side flexed and projecting into the effluent channel 61. The liquid inside of the absorbing member 721 drops to the effluent region 76 due to its own weight. Reference numeral 77 in the drawing denotes a case body that forms the effluent region 76 while holding the absorbing member 721. Thus, it is only necessary that the effluent channel 6 have a constitution through which the liquid flows by the capillarity. The effluent channel 6 is not limited to a glass pipe but may be a channel formed of a channel forming member.

Further, in the detection of the sensing object using the sensing sensor 2 of this disclosure, after supplying the sample solution to the sensing sensor 2, supply liquid that contains sensitizer (sensitizing liquid) combining with the sensing object adsorbed to the adsorbing film can be supplied. Further, sensitizing liquid containing sensitizer to be combined with the sensitizer thus combined with the sensing object is additionally supplied, thus allowing sensitizing. In the case where this sensitizing liquid is thus employed as well, mix with the liquid previously supplied when the sensitizing liquid is supplied to the channel is prevented, thus preventing dilution of the sensitizing liquid. This promptly combines the sensitizer, allowing enhancing the sensitivity of measurement and reducing lengthening of the measurement time.

Further, the crystal resonators 4A and 4B may be constituted of divided crystal elements. The respective crystal elements may be disposed significantly close to one another. Further, disposing the first crystal resonator 4A and the second crystal resonator 4B is not always required. One crystal resonator that includes an adsorbing film may be disposed. This is because of the following reason. When the adsorbing film adsorbs a sensing object, an oscillation frequency changes. Therefore, for example, if a threshold is preliminarily set, the presence/absence of the sensing object can be detected by determining whether the oscillation frequency exceeds the threshold or not.

Evaluation Test

Actually, the above-described sensing sensor 2 illustrated in FIG. 2 to FIG. 5 was manufactured. A colored sample solution was supplied to the liquid receiving portion 23. Then, a state that the sample solution flowed through the inside of the sensing sensor 2 was visually checked. The upper side cover body 21 was formed of a transparent body made of polycarbonate (PC). The channel Ruining member 5 was formed of a transparent body made of PDMS. The effluent channel 6 was formed of a glass pipe. The respective inlet side capillary member 55 and outlet side capillary member 56 were made of PVA. The capillary sheet 71 was made of PVA. The absorbing member 72 was formed of sponge made of PVA. The shape and the dimensions of these members were as described in the above-described embodiment. A total internal volume of a passing channel of the sample solution from the inlet side capillary member 55 through the channel 57 and the outlet side capillary member 56 and then reaching the downstream end of the effluent channel 6 was set to 40

Then, the sample solution of 80 µl, which is greater than the total internal volume, was supplied to the liquid receiving portion 23. Then, it was recognized that the sample solution passed through in the order of the inlet side capillary member 55→the channel 57→the outlet side capillary member 56→the effluent channel 6, flowed from the effluent channel 6 to the capillary sheet 71, and finally was absorbed into the absorbing member 72. It was also confirmed that when the all sample solution in the liquid receiving portion 23 flowed to the inlet side capillary member 55, a gap was formed between the capillary sheet 71 and the sample solution inside of the effluent channel 6, and the sample solution was divided between the capillary sheet 71 side and the channel 57 side. It was recognized that the sample solution in the capillary sheet 71 was absorbed into the absorbing member 72 before reaching the other end side of the capillary sheet 71.

The sensing device of this disclosure includes the sensing sensor and the measuring apparatus.

With the sensing sensor according to the embodiment, a sample solution flows from an injection port to an effluent channel via a channel at one surface side of a piezoelectric resonator. An adsorbing film disposed at the piezoelectric resonator adsorbs a sensing object contained in the sample solution. The sample solution is discharged from the channel to the effluent channel and is absorbed into an absorbing member via a capillary member. The capillary member is disposed in contact with a sample solution inside of the effluent channel. When the sample solution inside of the effluent channel reaches the capillary member, the sample solution moves so as to be pulled by the capillary member. This forms a gap between the capillary member and the sample solution inside of the effluent channel. Accordingly, a state where the capillary member and the channel that accumulates the sample solution is separated is likely to be formed. Therefore, even if a buffer solution is supplied in the sensing sensor prior to the sample solution, dilution of the sample solution by the buffer solution is reduced, thus allowing reducing deterioration of measurement sensitivity.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A sensing sensor, comprising:
   a wiring board that includes a connecting terminal to be connected to a measuring apparatus for measuring an oscillation frequency, and a depressed portion is formed at one surface side of the wiring board;
   a piezoelectric resonator that includes a piezoelectric piece and an excitation electrode disposed at the piezoelectric piece, the piezoelectric resonator covering the depressed portion, the piezoelectric resonator being secured to the wiring board such that a vibrating region is opposed to the depressed portion, the excitation electrode being electrically connected to the connecting terminal, the piezoelectric resonator including an adsorbing film configured to adsorb a sensing object in a sample solution at one surface side of the piezoelectric piece;
   a channel forming member disposed so as to cover a region at one surface side of the wiring board including the piezoelectric resonator, the channel forming member including an injection port for a sample solution;
   a channel formed between the wiring board and the channel forming member, the channel being configured to cause the sample solution supplied to the injection port to flow through from a one end side to another end side at the one surface side of the piezoelectric resonator;
   an effluent channel disposed at a downstream side of the channel, the effluent channel being configured to discharge the sample solution inside of the channel by capillarity;
   a capillary member having a flat surface parallel to the effluent channel and disposed at a downstream side of the effluent channel in contact with the sample solution flowing through an inside of the effluent channel, where one end side of the capillary member projecting from a downstream end of the effluent channel into a portion of an opening of the effluent channel, the capillary member being configured to cause the sample solution to flow through by the capillarity; and
   an absorbing member disposed at a downstream side of the capillary member, the absorbing member being configured to absorb the sample solution flowing through the capillary member.

2. The sensing sensor according to claim 1, wherein the sensing sensor is configured such that when the sample solution inside of the effluent channel reaches the capillary member, the sample solution moves to the capillary member side at a speed faster than a moving speed of the sample solution flowing through the effluent channel.

3. The sensing sensor according to claim 1, wherein the effluent channel is constituted of a glass pipe.

4. The sensing sensor according to claim 1, wherein the capillary member is formed into a sheet shape.

5. The sensing sensor according to claim 4, wherein when viewed in a planar surface, the sheet-shaped capillary member has a shape where one end side is narrower than another end side.

6. The sensing sensor according to claim 1, wherein the injection port is constituted of a hole of a porous capillary member.

7. The sensing sensor according to claim 1, further comprising:
   a porous capillary member disposed between the channel and the effluent channel,
   the porous capillary member being configured to cause the sample solution inside the channel to flow through the effluent channel by the capillarity.

8. A sensing device, comprising:
   the sensing sensor according to claim 1, and
   the measuring apparatus.

* * * * *